United States Patent [19]

Jacobsen

[11] Patent Number: 4,644,651
[45] Date of Patent: Feb. 24, 1987

[54] INSTRUMENT FOR GRIPPING OR CUTTING

[75] Inventor: Stephen C. Jacobsen, Salt Lake City, Utah

[73] Assignee: Jacobsen Research Corp., Salt Lake City, Utah

[21] Appl. No.: 798,840

[22] Filed: Nov. 18, 1985

Related U.S. Application Data

[63] Continuation of Ser. No. 591,269, Mar. 19, 1984, abandoned.

[51] Int. Cl.$^4$ ............................................. B65B 13/00
[52] U.S. Cl. ......................................... 30/251; 30/124; 30/262; 128/318; 128/321; 128/751; 292/108; 292/210; 294/104
[58] Field of Search ...................... 30/124, 251, 262; 294/11, 104; 292/108, 155, 210; 280/615; 128/731, 305, 318, 321

[56] References Cited

U.S. PATENT DOCUMENTS

| 554,433 | 2/1896 | Young | 30/251 |
| 877,220 | 1/1908 | Nilsson | 30/251 X |
| 1,531,688 | 3/1925 | Bush | 30/251 |

Primary Examiner—Douglas D. Watts
Attorney, Agent, or Firm—Thorpe, North & Western

[57] ABSTRACT

An instrument for cutting, gripping or clamping includes a base arm with a fixed jaw at one end thereof, and a movable jaw pivotally attached to the arm adjacent the fixed jaw. Also included is a shank, one end of which is pivotally connected to the movable jaw, with the shank extending generally parallel to the arm over its full length. An elongated handle which overlies the shank includes a laterally extending section which is pivotally connected to the other end of the arm and to the other end of the shank. When the handle is pivoted toward the shank, the movable jaw is caused to pivot toward the fixed jaw, and when the handle is pivoted away from the shank, the movable jaw is caused to pivot away from the fixed jaw.

16 Claims, 7 Drawing Figures

INSTRUMENT FOR GRIPPING OR CUTTING

This application is a continuation of application Ser. No. 591,269, filed Mar. 19, 1984, now abandoned.

BACKGROUND OF THE INVENTION

The present invention relates to a surgical/utility instrument and more particularly to an improved instrument which is easy to operate, manipulate and control.

Surgical instruments and tools in general which are to be held and manipulated by hand, such as forceps, needle holders, hemostats, scissors, metal cutters, etc., typically include scissor-like handles or gripping elements for actuating the instruments. In the surgical arts, see, for example, U.S. Pat. Nos. Gould—3,585,985; Thal—3,814,102; Williams—4,043,343; and Goald—4,369,788. The instruments of these patents each employs a pair of scissor-type handles to move a jaw actuating mechanism. Rings are provided on the end of each handle, one to receive the surgeons thumb, and the other to engage one or more fingers of the same hand. The jaws of the instruments are closed in each case by movement of either the fingers relative to the thumb, or alternatively, the thumb relative to the fingers. This type actuator mechanism allows the application of substantial force and has the advantage of familiarity to surgeons. However, such mechanisms are relatively clumsy, difficult to rotate and manipulate generally, occupy excessive space, are of limited sensitivity, and are complex and expensive to manufacture.

OBJECTS AND SUMMARY OF THE INVENTION

It is an object of the present invention to provide a new and improved instrument for gripping, sewing, clamping, or cutting which may be readily grasped, and manipulated, rotated, etc. with one hand.

It is another object of the invention to provide such an instrument which has a compact, narrow profile.

It is an additional object of the invention to provide a gripping, cutting or clamping instrument which may be held and used without blocking the user's view of the item or person being worked on.

It is also an object of the invention to provide an instrument which is highly sensitive to the user.

It is a further object of the invention to provide such an instrument which is simple in construction and inexpensive to manufacture.

The above objects are realized in a specific illustrative embodiment of the invention which includes a pair of mandible-like gripping or cutting elements which are actuated to move relative to one another by a pivotally mounted handle. The handle is coupled to one of the gripping or cutting elements by an actuator bar so that when the handle is pivoted in one direction, the gripping or cutting elements close, and when pivoted in the other direction, the elements open. The handle is elongated to extend generally parallel with and, in one embodiment, overlie the actuator bar, and this provides a compact, easily manipulated instrument. The handle and actuator bar are constructed so as to provide a large mechanical advantage to exert closing forces and yet they are operable under finger tip control for use on sensitive or fragile items.

In accordance with one aspect of the invention, a locking mechanism is provided with the instrument to enable locking the handle in a selected position. A variety of different locking mechanisms may be employed, all of which are operable under finger-touch control.

BRIEF DESCRIPTION OF THE DRAWINGS

The above and other objects, features and advantages of the invention will become apparent from a consideration of the following detailed description presented in connection with the accompanying drawings, in which.

DETAILED DESCRIPTION OF THE ILLUSTRATIVE EMBODIMENTS

Many of the disadvantages of the prior known forceps-gripper instruments are overcome in the present invention by provision of an alligator-jaw type instrument which is capable of finger tip control and is useable for a variety of purposes, such as, cutting forceps, hemostats, needle holders, tweezers, etc.

Figure 1:
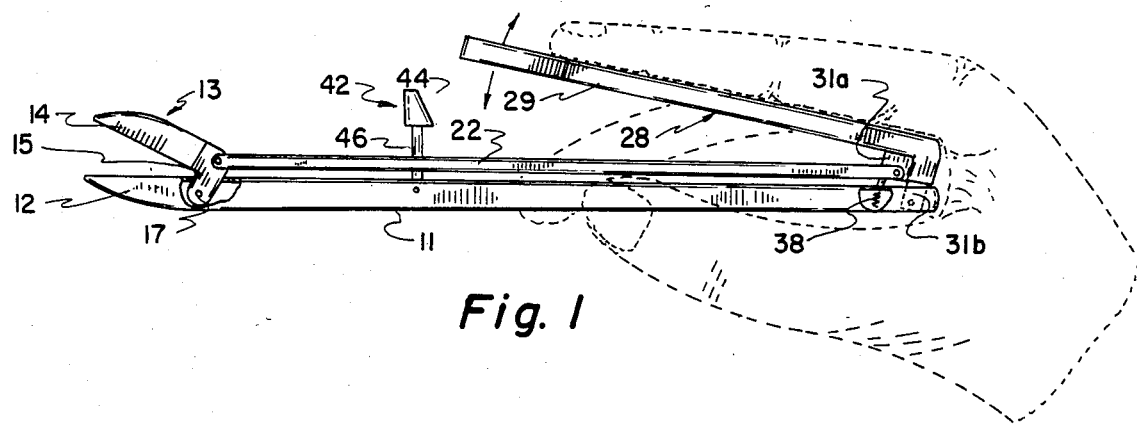
FIG. 1 is a side elevational, partially cut-away view of a forceps-gripper instrument made in accordance with the principles of the present invention.
Figure 2:
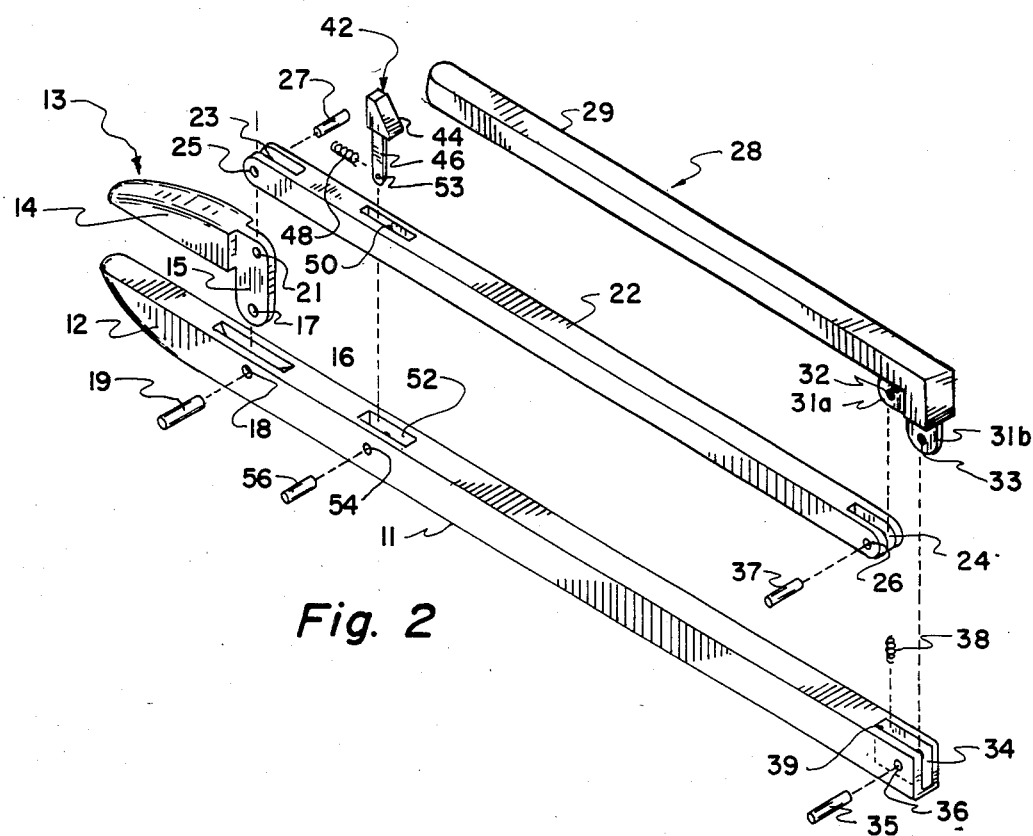
FIG. 2 is an exploded view in perspective of the instrument of FIG. 1.

Referring to FIGS. 1 and 2 of the drawings, there is shown a forceps-gripper instrument which includes a rigid base element or arm 11. One end of the arm 11 is formed into a lower jaw or gripper element 12. Although the lower jaw 12 is shown as being co-linear with the arm 11, the jaw could be formed to extend at any of a variety of angles from the arm, as desired by the user. Also, the jaw 12 could be formed into a cutting element rather than a gripping element as shown.

A moveable upper jaw structure 13 includes an upper jaw 14 and a laterally extending connecting member 15. The upper jaw is shaped to conform to and bear against the lower jaw. Again, however, the upper jaw 14 could be a cutting element rather than a gripping element. The connecting member 15 is formed integral with the jaw 14 and is flattened so as to be received within a slot 16 (FIG. 2) in the upper surface of the rigid arm 11. The lower edge of the member 15 is rounded and provided with an opening 17. A similar opening 18 extends transversely of the arm 11 and a pin 19 is received within the opening 17 and 18 to secure the member 15 within the slot 16.

The upper end of the member 15 is provided with another opening 21 which is spaced vertically from opening 17. An elongated actuating bar or shank 22 extends parallel to, and is spaced a short distance above, the arm 11. The opposite ends of the bar 22 are sloted, as at 23 and 24, and provided with openings 25 and 26. The upper, rear edge of the member 15 is received within the slot 23 and retained therein by a pin 27 inserted through the openings 25 and 21.

A handle 28 includes a lever section 29 and flat link sections 31a and 31b extending generally laterally thereof, with link section 31a being located above and forwardly of section 31b. The link sections 31a and 31b are formed integral with the lever 29, with section 31a having a rounded lower front edge and a transverse opening 32. Link section 31b has a rounded lower edge and a transverse opening 33. The opening 33 is close to the lower edge of section 31b and the vertical spacing between it and opening 32 is about the same as that between openings 17 and 21. A slot 34 is formed in arm 11 to receive the lower end of link section 31b and a pin 35 is inserted through a transverse opening 36 in the arm and opening 33 to retain the link section 31b in place. Link section 31a is positioned in a cavity 39 formed in the upper edge of the arm 11, and is compressed in the cavity by section 31a to bias the handle 28 upwardly. Of course, a variety of other spring mechanisms could also be utilized.

A latch 42 for holding the lever 29 close to the bar 22, and thus for holding the jaws 12 and 14 closed, includes a knob 44 mounted on the upper end of a post 46. The post 46 is fitted through an opening 50 in the bar 22 and into a cavity 52 formed in the arm 11. The lower end of the post 46 includes an opening 53 which, when the post is inserted in the cavity 52, aligns with an opening 54 in arm 11. A pin 56 is inserted in the openings 53 and 54 to hold the post 46 in place. A coil spring 48 is fitted in the cavity 52 against the post 46 to bias the post rearwardly away from the jaws 12 and 14. The latch 42 is positioned so that as the lever 29 is pivoted toward the bar 22, the distal end of the lever contacts a sloping rear surface of the knob 44, forcing the knob and post 46 forwardly. After the and of the lever is moved downwardly beyond the knob 44, the knob is forced rearwardly (by the spring 48) to overlie the end of the lever and lock it in place. The lever 29 is released by simply pushing the knob forwardly until the end of the lever clears the knob 44 and is forced upwardly by spring 38.

The arm 11, bar 22, member 15 and link 31 form a four bar linkage so that the short sides of the linkage, i.e., member 15 and link 31, can pivot about their connections toward the lower long side of the linkage, i.e., arm 11. Lever 29 is attached to link 31 such that when the lever is parallel to and overlies the bar 22, link 31 and member 15 are pivoted counterclockwise to clamp the upper jaw 14 against the lower jaw 12. When the lever is moved clockwise upwardly, link 31 and member 15 pivot in the same direction to move the upper jaw 14 away from the lower jaw 12 and thereby open the jaws.

The various elements of the instrument lend themselves to ease of manufacture. In particular, all of the elements may be readily injection molded.

In an exemplary operation of the instrument, the surgeon grasps the arm 11 with his thumb on one side and his middle and/or ring fingers on the other, and his index finger on the lever as illustrated in FIG. 1. This chopsticklike grip enables ready manipulation of the instrument while allowing the user to view the area to be worked on. With the jaws closed the instrument may be moved into position in an incision where it is wanted. The jaws may then be opened by deflecting the knob 39 with the tip of the index finger and allowing the force of spring 38 to pivot link 31 and the lever 29 clockwise. The rate and extent of opening can be controlled by pressure of the index finger on the lever. When the instrument is shifted to position an object between the jaws, the lever is depressed by the index finger causing link 31 and member 15 to pivot counterclockwise and close the jaws. If the instrument is used as a hemostat or as a tissue cutting forceps, sufficient force can be generated by pressure of the index finger. Since the lever 29 is several times longer than the distance between openings 32 and 33, the force exerted between the jaws is a corresponding multiple of the force applied on the lever. Pressure exerted by the jaw movement can be sensed through resistance to movement of the lever. Because the end of the index finger is itself sensitive, the resistance can be detected and assessed to control the pressure of the jaws. The spring loading of the lever causes the lever to follow the surgeons index finger in both directions until it is locked or released. It will be understood, of course, that the instrument could be grasped and handled in a variety of the other ways to suit the needs and comfort of the user.

To improve the delicacy of the instrument for grasping objects, the lever 29 could be made of an elastic material such as plastic. Then, the lever 29 would tend to bend when the jaws 12 and 14 encountered resistance in closing and this would serve to protect the object grasped from being crushed or damaged. Alternatively, the bar 22 could be made longitudinally elastic, for example, by use of a spring-loaded telescoping bar. This again would result in greater delicacy in grasping objects, and a more compliant grip.

Figure 3:
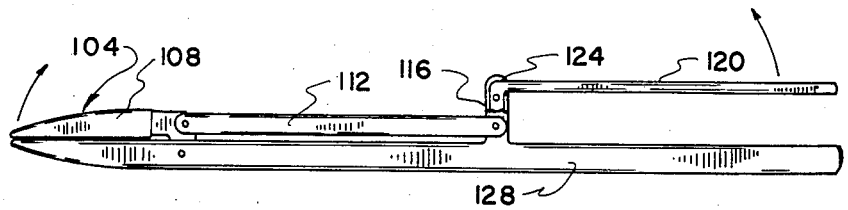
FIG. 3 is a side elevational view of another embodiment of the present invention.

FIG. 3 shows an alternative embodiment of the forceps-gripper instrument of the present invention. In this embodiment, the gripping or cutting end 104 of the instrument is constructed the same as that of the FIGS. 1 and 2 embodiment. An upper jaw 108, again, is connected to one end of an actuating bar or shank 112. The other end of the bar 112 is coupled to a link 116 which extends laterally of a lever 120. The lever 120 is pivotally mounted in a clevis 124 which extends upwardly from a base element of arm 128. The bar 112 is shorter than the bar 22 of FIGS. 1 and 2 and is coupled to the front end (rather than back end) of the lever 120. The lever 120 extends rearwardly, rather than forwardly as with the embodiment of FIGS. 1 and 2. The embodiment of FIG. 3 would be grasped in a manner similar to grasping pliers and thus would not be as easily manipulated, rotated and handled, in most uses, as would the embodiment of FIGS. 1 and 2.

Figure 4A:
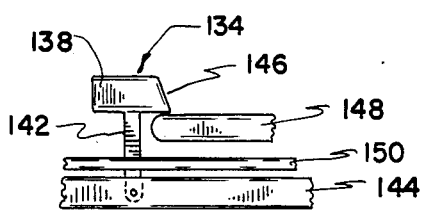
FIGS. 4A, 4B and 4C show three different alternative embodiments of locking mechanisms which may be employed in the instruments of FIGS. 1 and 2.
Figure 4B:
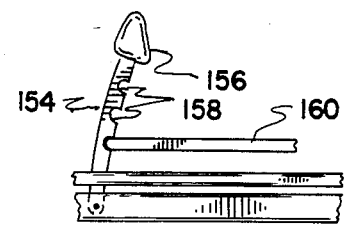
Figure 4C:
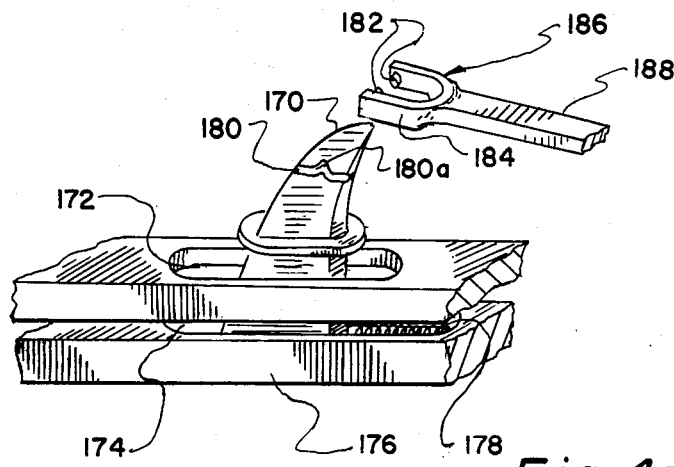

FIGS. 4A through 4C show different alternative embodiments for the latch 42 of FIGS. 1 and 2. In FIG. 4A, there is shown a rocker latch which includes a T-shaped holding member 134 having a head 138 positioned at the top of a post 142. The lower end of the post 142 is mounted in a slot in a base element or arm 144 to pivot forwardly and rearwardly. A back side 146 of the heat 138 is sloped so that when a lever 148 is pressed downwardly on the head, the member 134 is forced forwardly as the lever slides over the sloping side. When the lever 148 is pressed downwardly below the level of the head 138, a spring 150 forces the member 134 rearwardly so that the head 138 overlies and latches the lever 148 in place, as shown. To release the lever 148, the front side of the head 138 is pressed, causing member 134 to pivot forwardly and release the lever.

The FIG. 4B embodiment includes an elongated arcuate post 154 which includes a knob 146 having a sloping back side. Serrations or notches 158 are provided along the post to engage the end of a lever 160 and lock it in a range of positions. This allows the jaws to be locked in a number of positions from full closed to partially open depending upon the thickness of the tissue or object being gripped.

FIG. 4C shows a "push-push" type of latch which includes a camming head 170 mounted on a post 172 whose lower end is pivotally mounted in a slot 174 in a base element or arm 176, with the post being biased forwardly by a spring 178. A camming track 180 is formed on one side of the head 170 to receive a nipple 182 which extends transversely of one finger 184 of a U-shaped termination 186 of a lever 188. When the lever 188 is pressed downwardly, the nipple 182 slides over the front surface of the camming head 170 until it reaches the camming track 180. The nipple 182 then enters the track 180 and, when pressure on the lever 188 is released, moves to the peak location 180a of the track. This is the latch position of the lever 188. When the lever 188 is again pressed downwardly, the nipple 182 moves from the peak location 180a of the track 180 downwardly, rearwardly and then out of the track to thus release the lever so that it can pivot upwardly and out of contact with the head 170.

Figure 5:
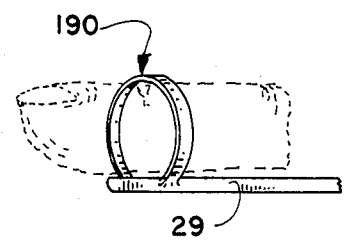
FIG. 5 shows an alternative embodiment of a handle which may be employed with the instruments of FIGS. 1 and 2.

FIG. 5 shows an alternative embodiment for the handle 28 of the FIGS. 1 and 2 instrument. Included on the end of the lever section 29 and formed integrally therewith to project upwardly is a ring 190 into which the end of a person's index finger, shown by dotted line, may be inserted when using the instrument. This gives the user positive control of the lever 29 for both downward and upward movement of the lever.

Since the present instrument is compact, it occupies a minimum space in the instrument tray and sterilizer as well as in the incision during an operation. The instrument can be readily inserted and used in small incisions where conventional scissors or forceps could not. The various parts of the instrument do not involve complex shapes and can thus be easily machined to the tolerances necessary. The cost of manufacture is therefore minimized.

While the invention has been described with reference to specifically illustrated preferred embodiments, it should be realized that various changes may be made without departing from the disclosed inventive subject matter particularly pointed out and claimed herebelow.

What is claimed is:

1. An instrument for gripping or cutting comprising
    an elongate base arm having a fixed jaw at a first end thereof which projects outwardly from the base arm,
    a movable jaw having a laterally extending member at a rear end of the jaw pivotally mounted on said arm adjacent the fixed jaw to pivot and cause the movable jaw to move toward the fixed jaw to a closed position and away from the fixed jaw to an open position, said movable jaw projecting outwardly generally parallel to and in close proximity or contact with the fixed jaw when in the closed position,
    a shank extending generally parallel to said arm, one end of which is pivotally connected to the movable jaw, and
    an elongated handle having a first laterally extending section at a rear end, said section being pivotally mounted on said arm at a second end thereof opposite the first end, said elongated handle having a second laterally extending section located forwardly of the first section and pivotally connected to the other end of the shank so that a forward end of the handle extends forwardly in an overlying relationship with the shank, and so that as the handle is pivoted toward the shank to a position generally parallel with the shank and arm, the shank is moved to cause the movable jaw to pivot to the closed position.

2. An instrument as defined in claim 1 further including first biasing means for normally biasing the handle to pivot away from the shank.

3. An instrument as defined in claim 2 further including a latch mounted to engage and hold the handle when it is pivoted to a position generally parallel with the shank.

4. An instrument as defined in claim 3 wherein the latch comprises
    a post mounted on the arm to move between a latch position and release position,
    a knob formed on top of the post to engage and hold the free end of the handle when the handle is pivoted to a position generally parallel with the shank and when the post is in the latch position, with the knob including a sloping rear surface over which the end of the handle may slide to force the knob and post forwardly toward the release position, and
    second biasing means for normally biasing the post and knob to the latch position.

5. An instrument as in claim 4 wherein said arm includes a cavity which faces upwardly for receiving the lower end of the post, and wherein said shank includes an opening positioned above and generally in line with the cavity, said post being mounted to extend from the cavity through the opening.

6. An instrument as in claim 3 wherein the latch comprises
    an arcuate post mounted on the arm to extend toward the handle and to move between a latch position and a release position, said post including a plurality of notches spaced apart longitudinally along one side of the post to engage and hold the free end of the handle in a selectable one of a plurality of positions defined by the notches, and
    second biasing means for normally biasing the post to the latch position.

7. An instrument as in claim 6 wherein said arm includes a cavity which faces upwardly for receiving the lower end of the post, and wherein said shank includes an opening positioned above and generally in line with the cavity, said post being mounted to extend from the cavity through the opening.

8. An instrument as in claim 3 wherein the latch comprises
    a post mounted on the arm to pivot between a latch position and release position,
    a head formed on top of the post and having a forward projection and a rearward projection, with the rearward projection including a sloping rear surface over which the end of the handle may slide to force the head and post forwardly toward the release position to allow the end of the handle to slip under the rearward projection to be held thereby, said head and post pivoting forwardly to release the handle when the forward pojection is pressed, and
    second biasing means for normally biasing the post and head to the latch position.

9. An instrument as in claim 8 wherein said arm includes a cavity which faces upwardly for receiving the lower end of the post, and wherein said shank includes an opening positioned above and generally in line with the cavity, said post being mounted to extend from the cavity through the opening.

10. An instrument as in claim 3 wherein said latch comprises a camming element formed on the end of the handle, a post mounted on the arm to move between a latch position and release position, and a head formed on top of the post and having a camming track formed therein for receiving the camming element when the handle is first pivoted toward the shank, and for releasing the camming element when the handle is next again pivoted toward the shank.

11. An instrument as in claim 10 wherein said arm includes a cavity which faces upwardly for receiving the lower end of the post, and wherein said shank includes an opening positioned above and generally in line with the cavity, said post being mounted to extend from the cavity through the opening.

12. An instrument as in claim 1 wherein said handle is constructed of an elastic material to allow resilient bending of the handle.

13. An instrument as in claim 1 wherein said shank is constructed of an elastic material to allow resilient longitudinal flexing of the shank.

14. An instrument as in claim 1 wherein the fixed jaw and moveable jaw are formed to extend at an angle to the arm and shank.

15. An instrument as in claim 1 further including an annular element positioned on top of the handle at the free end thereof for receiving the end of a person's finger with the handle being generally perpendicular to the place defined by the annular element.

16. An instrument for gripping or cutting comprising
- an elongate base arm having a fixed jaw at one end thereof,
- a movable jaw having a laterally extending member at a rear end of the jaw pivotally mounted on said arm adjacent the fixed jaw to pivot and cause the movable jaw to move toward and away from the fixed jaw,
- a bar extending generally parallel to said arm, one end of which is pivotally connected to the rear end of the movable jaw, and
- an elongated handle having a first laterally extending section at a rear end, said section being pivotally mounted on said arm at a location spaced from the location at which the movable jaw is mounted to the arm, said elongated handle having a second section extending laterally in the same direction as the first section but not as great a distance as and forwardly of the first section, said second section being pivotally connected to the other end of the bar so that a forward end of the arm is pivotable forwardly and downwardly toward the arm to move the bar forwardly and cause the movable jaw to pivot toward the fixed jaw.

* * * * *